(12) United States Patent
Carusillo et al.

(10) Patent No.: US 6,960,894 B2
(45) Date of Patent: Nov. 1, 2005

(54) CORDLESS, POWERED SURGICAL TOOL

(75) Inventors: Steve Carusillo, Kalamazoo, MI (US);
David M. Nic, Vicksburg, MI (US);
Chris Philipp, Portage, MI (US);
James G. Walen, Kalamazoo, MI (US)

(73) Assignee: Stryker Corporation, Kalamazoo, MI (US)

(*) Notice: Subject to any disclaimer, the term of this patent is extended or adjusted under 35 U.S.C. 154(b) by 147 days.

(21) Appl. No.: 10/210,325

(22) Filed: Aug. 1, 2002

(65) Prior Publication Data
US 2004/0022527 A1 Feb. 5, 2004

(51) Int. Cl.[7] ............................................. H02P 1/18
(52) U.S. Cl. .................. 318/138; 318/254; 318/439; 318/432; 318/434; 318/461; 388/800; 388/804; 388/816; 388/937
(58) Field of Search .................... 318/139, 255, 318/268, 798, 799, 807, 810, 811, 432, 434, 138, 254, 439, 461; 388/800–804, 806, 816, 937; 606/32, 82

(56) References Cited

U.S. PATENT DOCUMENTS

| | | | |
|---|---|---|---|
| 3,611,095 A | * 10/1971 | Schnizler ..................... 318/305 |
| 3,988,656 A | * 10/1976 | Schnizler, Jr. et al. ...... 318/345 |
| 4,307,325 A | * 12/1981 | Saar | |
| 4,494,057 A | 1/1985 | Hotta | |
| 4,513,381 A | * 4/1985 | Houser, Jr. et al. ......... 364/475 |
| 5,014,793 A | * 5/1991 | Germanton et al. .......... 173/12 |
| 5,268,622 A | * 12/1993 | Philipp ........................ 318/254 |
| 5,414,793 A | * 5/1995 | Morikawa .................... 388/824 |
| 5,747,953 A | 5/1998 | Philipp | |
| 5,804,936 A | * 9/1998 | Brodsky et al. ............. 318/254 |
| 5,901,269 A | * 5/1999 | Chang ........................ 388/832 |
| 6,013,991 A | 1/2000 | Philipp | |
| 6,025,683 A | 2/2000 | Philipp | |
| 6,037,724 A | 3/2000 | Buss et al. | |

FOREIGN PATENT DOCUMENTS

EP 0633095 A1 1/1995
EP 0680808 A1 11/1995

* cited by examiner

Primary Examiner—Rina Duda
(74) Attorney, Agent, or Firm—Flynn, Thiel, Boutell & Tanis, P.C.

(57) ABSTRACT

A powered tool for performing surgical procedures. The tool includes a handpiece in which a power generating unit is housed. A control member is mounted to the handpiece. The control member is mounted to the handpiece so that the orientation of the control member can be selectively set relative to the point to which it is mounted to the handpiece and so it can move relative to a reference point on the handpiece. A control module monitors the orientation of the control member and its position relative to the reference point. Based on the control member orientation and position, the control module generates signals to regulate the operation of the power generating unit. When the power generating unit is a motor, the control module generates signals to ensure that the maximum speed at which the motor can be driven is less than the no load speed.

35 Claims, 11 Drawing Sheets

CORDLESS, POWERED SURGICAL TOOL

FIELD OF THE INVENTION

The invention of this application relates generally to a cordless, battery operated powered surgical tool. More particularly, the invention of this application relates to a cordless powered surgical tool, such as a surgical saw, that can be selectively configured for the preferences of individual surgeons and that is relatively quiet to operate.

BACKGROUND OF THE INVENTION

The cordless powered surgical tool has become an important instrument for performing a number of different surgical procedures. Generally, this tool includes a handpiece in which an electrically driven motor is housed. Power to energize the motor is supplied by a battery that is usually removably attached to the handpiece. A gear assembly and a coupling assembly transfer the rotary power developed by the motor to a cutting accessory. Typically, the coupling assembly is designed to removably hold the cutting accessory to the rest of the tool. Generally these tools, like other tools are used for separating and or removing hard and/or soft tissue from a patient.

A cordless powered surgical tool, as the name implies, does not have a cord to serve as a power conduit from an external source. This eliminates the need for surgical personnel to concern themselves with sterilizing a cord so that it can enter a sterile surgical field during a surgical procedure and/or ensuring that during a surgical procedure an unsterilized cord is not inadvertently brought into the surgical field. Another benefit a cordless surgical tool offers is that the elimination of the cord result in the like elimination of the physical clutter and field-of-view blockage the cord otherwise brings to a surgical procedure.

The Applicant's U.S. Pat. No. 5,747,953, CORDLESS, BATTERY OPERATED SURGICAL TOOL, issued May 5, 1998, and incorporated herein by reference, discloses a trigger assembly and control circuit suitable for integration into a cordless surgical tool. The particular tool described in this document is a drill. This type of tool has a linkage and a coupling assembly that are positioned to cause a drill bit to be driven in a rotary motion. The trigger assembly disclosed in this patent has two triggers. Collectively, the trigger assembly and control circuit are configured so that depression of one trigger will cause the motor shaft to rotate in a first direction, arbitrarily, forward rotation. Depression of the second trigger will cause the motor shaft to rotate in a second direction, arbitrarily, reverse rotation. The trigger assembly and control circuit are further configured so that simultaneous depression of both triggers will result in current being supplied to the motor in such a pattern that it oscillates in forward-reverse-forward-reverse movement.

The assembly disclosed in U.S. Pat. No. 5,747,953 has proven quite useful in many powered surgical tools. It has proven especially useful for integration in powered surgical tools that have tissue working cutting accessories that are designed to rotate around their longitudinal axes. Accessories that are so driven include drill bits and wires which are driven by drills and/or wire drivers.

However, there are limitations associated with other cordless surgical tools, specifically, saws. Generally, a powered surgical saw is a powered surgical tool with a linkage that causes the associated coupling assembly to move in a repetitive back-and-forth pattern. The coupling assembly holds a blade that is designed to cut tissue. Some saws have a linkage assemblies designed to move the complementary saw blades back and forth in a reciprocating pattern, along the longitudinal axes of the associated blades. Other saws have linkage assemblies that move the associated blades in a sagittal or oscillating movement, specifically so that the blades pivot back and forth.

One of these limitations is associated with the fact that, by the very nature of its method of use, a saw blade engages in repetitive back and forth action. As a result of this motion, the blade is invariably repetitively forced against components of the coupling assembly that holds the blade to the saw. Components forming the linkage assembly and coupling assembly similarly repetitively contact each other as a result of the bi-directional movement in which these components engage. This component contact results in an appreciable amount of noise being generated when a saw is actuated. This noise, at a minimum, can make it difficult to hear other sounds in an operating room. This noise can further be distracting to the surgeon and serve as one of the environmental factors that contribute to the stress surgical personnel experience when performing a procedure.

One means by which surgical personnel have tried to reduce the noise developed by a saw or other powered surgical tool is to run the tool at less than its highest speed. Typically this is the free speed, the no load speed, of the motor integral with the tool. Typically, this speed control is performed by manually depressing the trigger integral with the tool so that it is only partially depressed. Often a surgeon will operate the tool in this manner in the short time period before the associated cutting accessory is pressed against the tissue the accessory is intended to work. Then, as the motor speed drops as a consequence of the motor developing torque, the surgeon will adjust the pressure placed on the trigger to maintain the operation of the motor at the desired speed. While this method has proven somewhat successful in reducing tool-generated noise, it requires the surgeon to concentrate on the extent he/she has depressed the trigger integral with the tool. Thus, the surgeon has to devote some attention to the trigger setting; this may distract from the surgeon's ability to concentrate on other aspects of performing the surgical procedure.

Another method some surgeons find useful in reducing tool noise is to perform the surgical procedure with a slower speed tool. This type of tool, in comparison to its higher speed counterpart, generates less noise. It should also be apparent that, in comparison to a high speed tool, the lower speed tool is less powerful and may not be able to cut tissue as fast. In some instances, the lower speed tool may not even have the power to perform the task that can be accomplished with the higher speed tool. Consequently, in a facility where surgeons find a lower speed tool useful, the facility typically also finds it desirable, if not necessary, to also have the higher speed tool available. This latter tool is thus present for use by surgeons that prefer its faster operation and do not object to the noise. It is also necessary to have the higher speed tool ready for situations where it can perform tasks that are difficult, if not impossible, to accomplish with the lower speed unit. This essentially requires the hospital or other surgical facility to, in a sense, double the number of tools it has available in order to accommodate for the preferences of individual surgeons. This near duplication adds to the expense associated with providing a surgical facility.

SUMMARY OF THE INVENTION

This invention relates to a cordless powered surgical tool with a control assembly that governs the initial operating speed of the tool so as to reduce the noise generated by the tool and the wear to which its components are exposed. This invention also relates to a control assembly for a surgical tool that has a trigger assembly that allows the surgeon to easily select the maximum speed of the tool.

BRIEF DESCRIPTION OF THE DRAWINGS

The invention is pointed out with particularity in the claims. The above and further features and benefits of the invention may be better understood by reference to the following description take in conjunction with the accompanying drawings in which:

DETAILED DESCRIPTION

Figure 1:
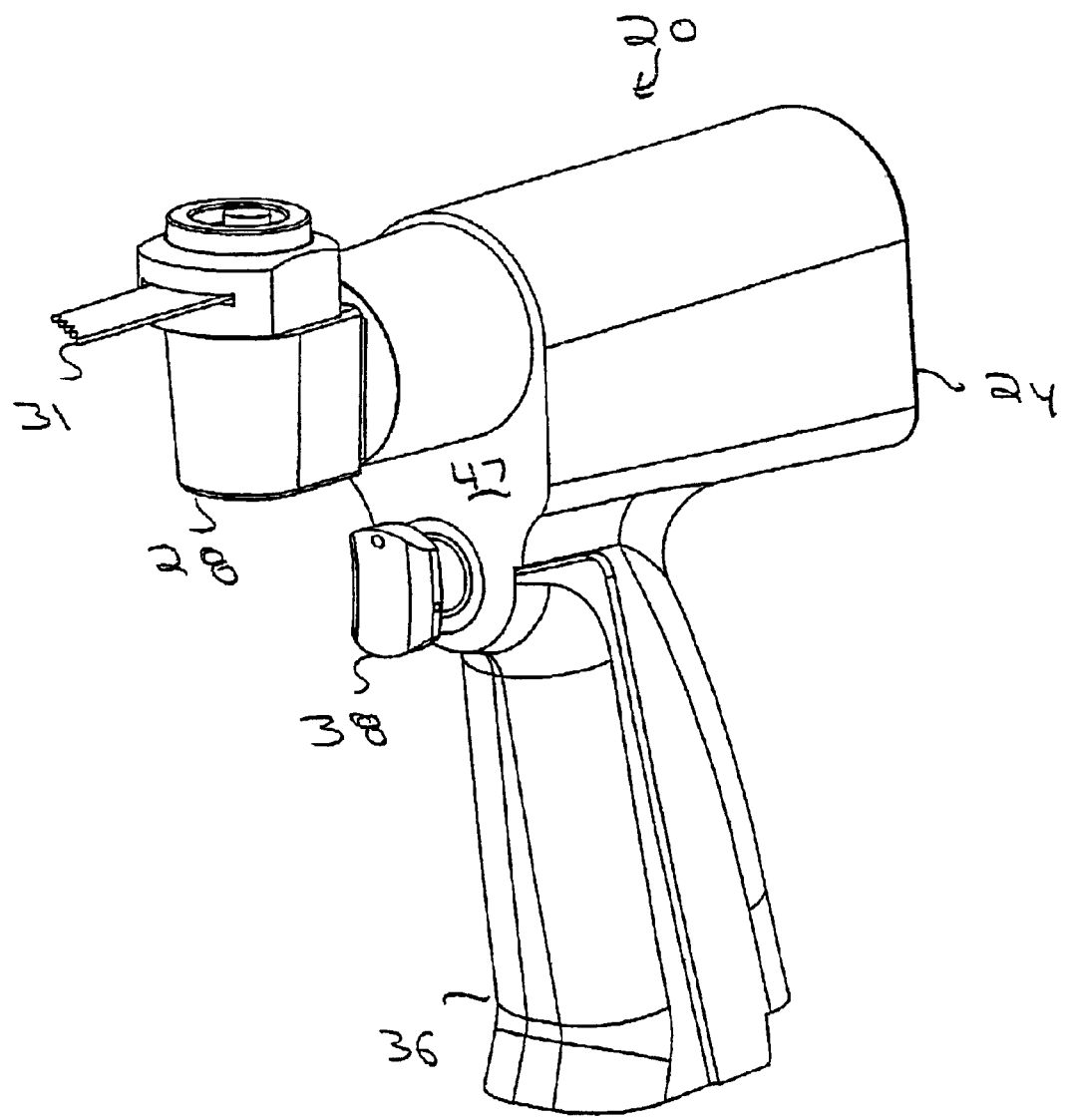
FIG. 1 is a perspective view of a cordless powered surgical tool into which the features of this invention are incorporated.
Figure 2:
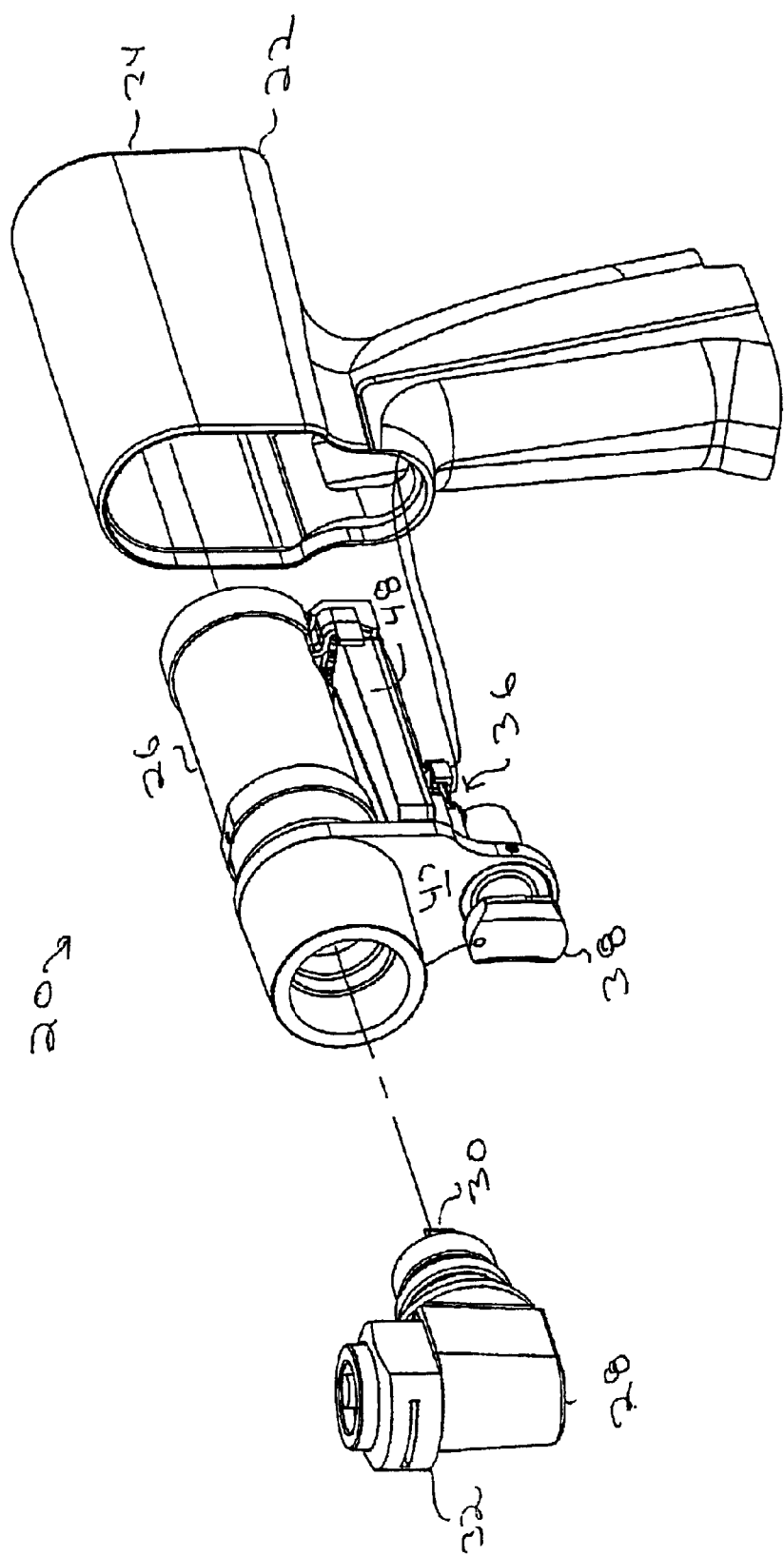
FIG. 2 is an exploded view of the tool of FIG. 1.

FIGS. 1 and 2 illustrate the basic features of a powered surgical tool 20 that is constructed in accordance with this invention. Tool 20 is a sagittal saw. It should, of course be recognized that other tools such as reciprocating saws, drills, reamers and wire drivers may embody the features of this invention. Tool 20 includes a housing 22 that contains most of the other components of the tool. Housing 22 has an upper portion 24 in which contains a DC driven, variable speed motor 26. A sagittal head 28 extends forward from an opening in the housing upper portion 24. Fitted to the sagittal head 28 are a linkage assembly 30 and a coupling assembly 32. The linkage assembly 30 is connected to the output shaft of the motor 26 and the coupling assembly 32. The linkage assembly 30 transfers and converts the rotary motion of the motor shaft to the coupling assembly so that the coupling assembly moves in an oscillatory pattern. The coupling assembly 32 is designed to releasably hold a saw blade, not illustrated, so that the blade engages in a like oscillatory motion with the coupling assembly.

Figure 3:
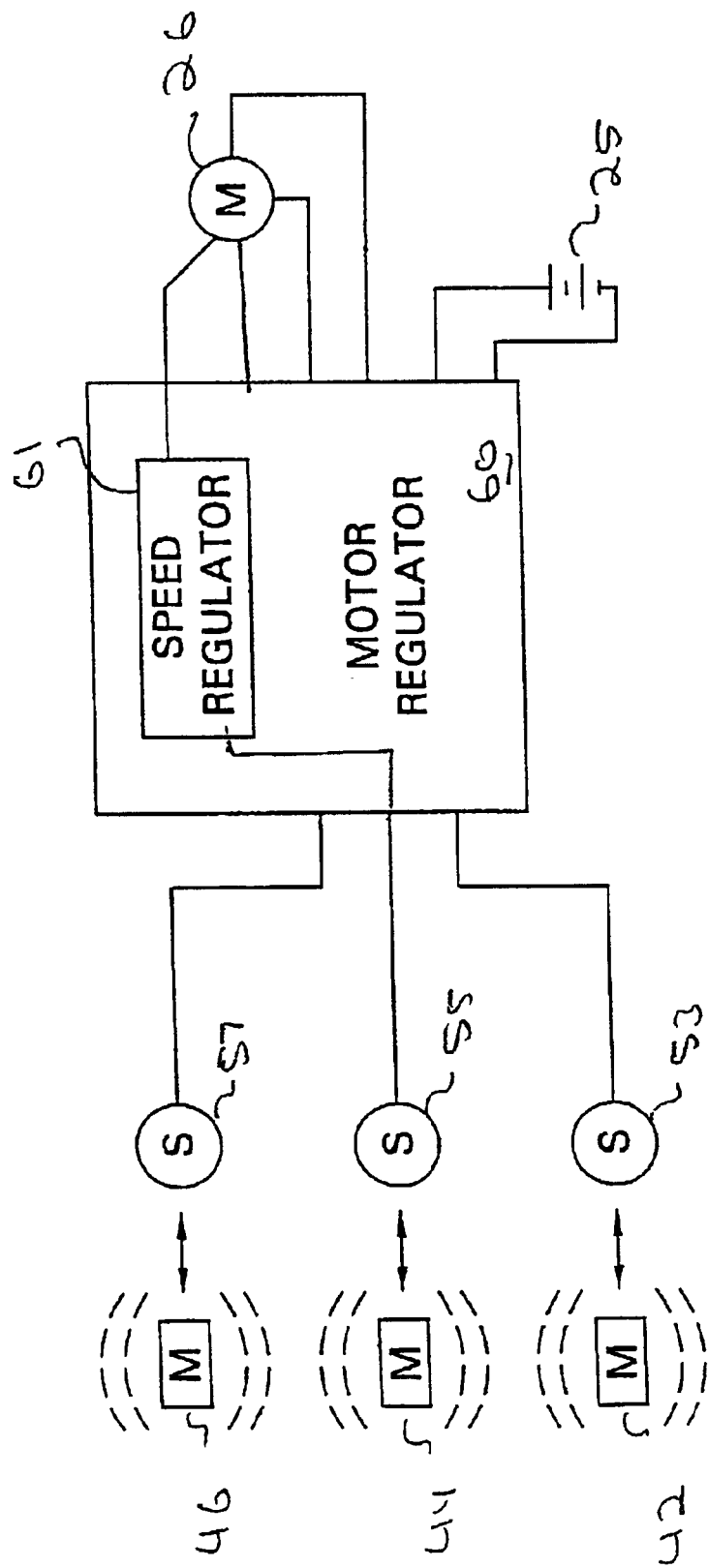
FIG. 3 is a diagrammatic and block diagram of the control circuit of the powered surgical tool of this invention.

Housing 22 is further formed to have a handgrip 34 that extends below the upper portion 24. A battery 25, depicted in FIG. 3, for providing an energization current to the motor 26 is removably attached to the base of handgrip 34. A controller 36 regulates the actuation of the motor 26. Controller 36 includes a moveable trigger 38 that extends forward from housing 22. Located inside the housing 22 immediately above the trigger 38 is a carriage assembly 40. Trigger 38, in addition to being slidable in and out of the housing 22, can also be rotated relative to the housing. Three magnets 42, 44 and 46 (FIG. 7A) are moveably mounted to the carriage assembly 40. The trigger and carriage assemblies, 38 and 40, respectively, are connected so that depression of the trigger results in the displacement of two of the three magnets 42, 44 and 46. Which two of the magnets are actuated is a function of the rotational orientation of the trigger 38 relative to the housing 22.

More particularly, the housing 22 is formed so that the forward facing end of upper portion 24 is open. A face plate 47 is seated in this opening. Face plate 47 is the structural member of the tool 20 to which motor 26, sagittal head 28, trigger 38 and carriage assembly 40 are mounted.

The control assembly 36 also includes a sealed module 48 located in the housing 22 above the carriage assembly 40. Internal to sealed module 48 is a control circuit for regulating the actuation of the motor 26. This control circuit is generally described by reference to FIG. 3. In one version of the invention, the control circuit includes three sensors 53, 55 and 57. Each sensor is seated in the module 48 so as to be located in the path of travel of a separate one of the magnets 42, 44 and 46, respectively. Each sensor 53, 55 and 57 generates a signal representative of the strength of the magnetic field generated by the associated magnet 42, 44 and 46, respectively. In one version of the invention, sensors 53, 55 and 57 are Hall effect sensors. The signals generated by the sensors 53, 55 and 57 are applied to a motor regulator 60, also part of the control circuit.

Motor regulator 60, based on the signals generated by the sensors 53, 55 and 57, controls the application of current to the windings integral with motor 26 so as to regulate the actuation of the motor and the speed with which the motor shaft rotates. Generally, it should be understood that sensor 53, the sensor associated with magnet 42 generates a signal indicating whether or not the motor is to be actuated so its shaft rotates in a first direction, arbitrarily for this purpose, being called the forward direction. Sensor 57, the sensor associated with magnet 46, the magnet furthest from magnet 42, generates a signal indicating whether or not the motor should be actuated so that the shaft rotates in a reverse direction opposite the forward direction. Sensor 55, the sensor associated with center-located magnet 44, generates a signal indicating the speed at which the motor is to be driven. Based on these signals, motor regulator 60 selectively applies current to the windings of the motor so as to cause the rotation of the shaft in the desired direction and at the desired speed.

Internal to the motor regulator 60, it should be understood that there is circuitry that comprises a speed regulator 61. The speed regulator 61 is connected to the motor 26 for monitoring the speed of the motor. In motors with sensors, for example, Hall sensors, the speed regulator 61 monitors the output signals generated by those sensors. In sensorless motors, speed regulator 61 is connected to the windings of the motor to monitor the back EMF pulses. A component internal to the speed regulator 61 includes a tachometer for, in response to the signals received from the motor, generating a signal representative of shaft speed. The speed regulator 61 also includes some sort of comparator that compares the motor speed to the user-selected speed for the motor. The output signal generated by the comparator is thus used by other circuitry internal to the motor regulator 60 to cause current to be flowed to the motor at an appropriate rate to ensure that the motor shaft, to the extent possible, is rotated at the user selected speed.

A detailed discussion of the control circuit including both the motor regulator 60 and speed regulator 61 is found in U.S. Pat. No. 5,747,953 which is incorporated herein by reference. Alternative circuit components for the motor regulator are found in U.S. Pat. No. 6,025,683, MOTOR CONTROL CIRCUIT FOR REGULATING A DC MOTOR, issued Feb. 15, 2000 and incorporated herein by reference.

As discussed above, the above motor regulator 60 is constructed to actuate the associated motor 26 in either a forward or reverse direction. The power tool 20 of the described version of the invention is a saw. Linkage assembly 30 is capable of transferring the rotational moment of the motor shaft, regardless of the forward or reverse state of this moment into oscillatory motion. Therefore, for the purposes of this particular type of power tool constructed in accordance with this invention, the fact that the motor can be actuated so that its shaft rotates in either a forward or reverse direction is not relevant.

Figure 4A:
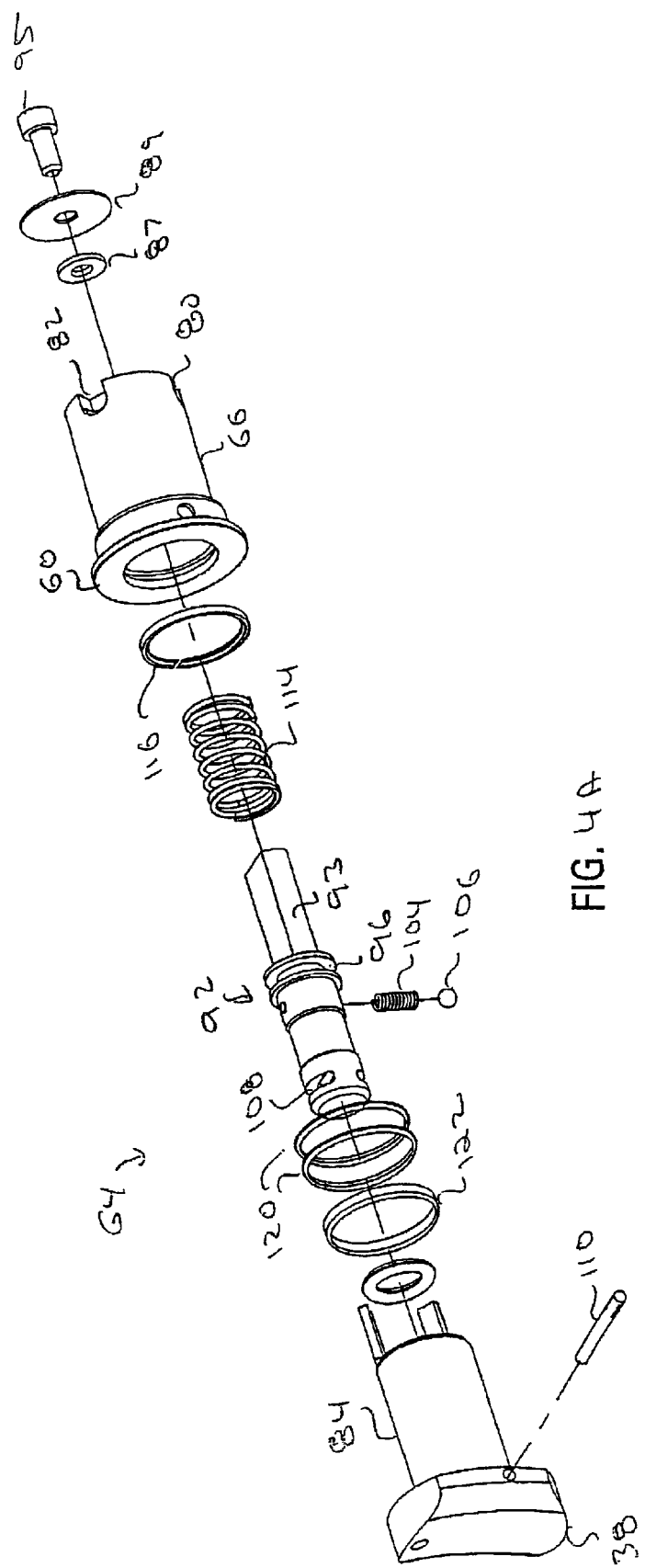
FIGS. 4A and 4B are, respectively, exploded and cross-sectional views of the trigger assembly.
Figure 4B:
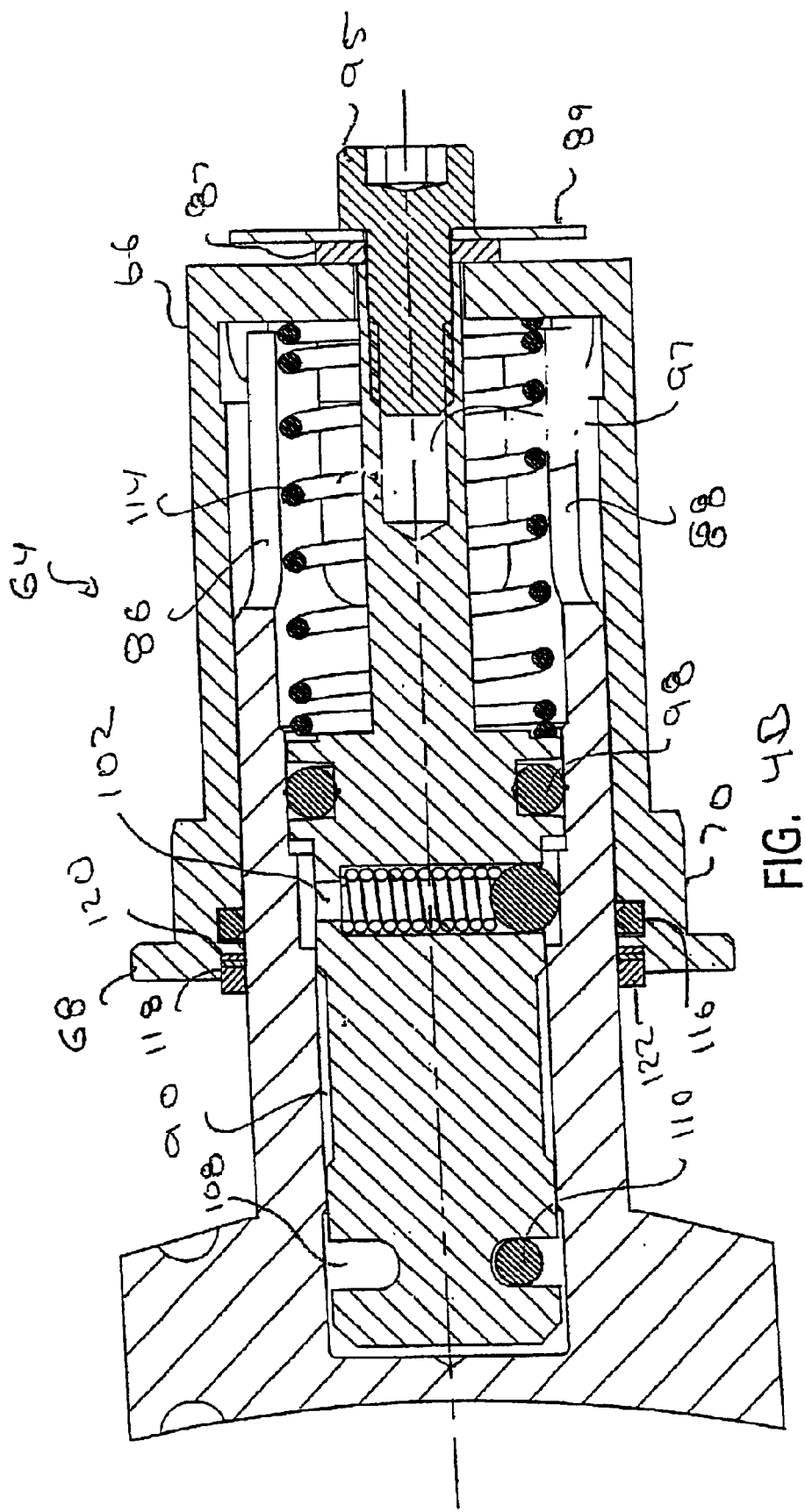
Figure 5:
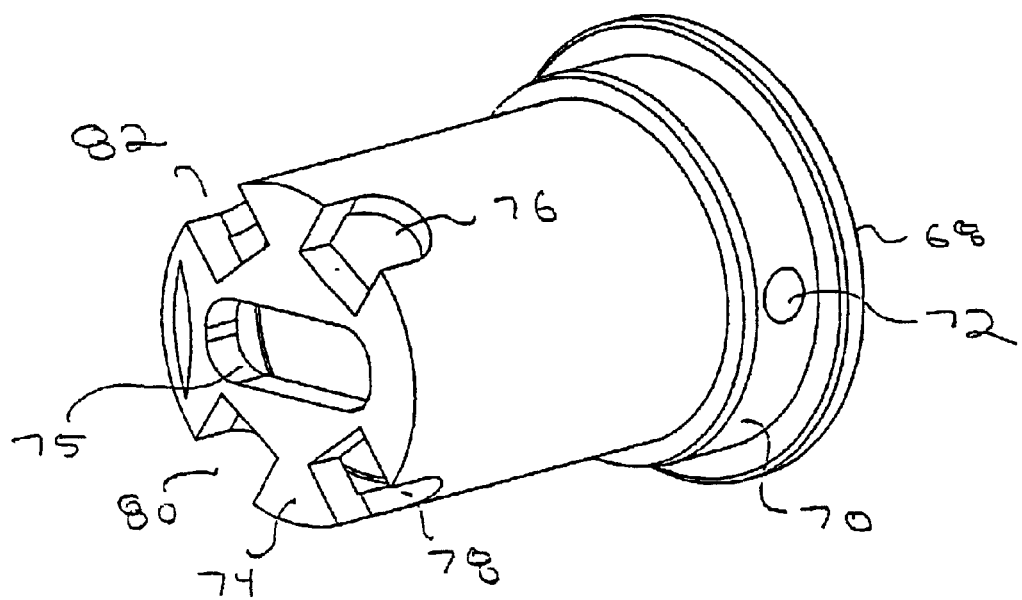
FIG. 5 is a perspective view of the proximal facing end of the shaft housing of the trigger assembly.

Trigger 38 is part of a trigger assembly 64 now described by initial reference to FIGS. 4A and 4B. The trigger assembly 64 includes a generally cylindrically shaped shaft housing 66, now described by reference to FIG. 5. Shaft housing 66 is closed at its proximal end and open at its distal end. ("Proximal" shall be understood to be towards the end of the tool facing the surgeon; "distal" is understood to be towards the surgical site to which the tool is applied.) Shaft housing 66 is further formed so as to have a flat, circumferentially extending lip 68 that extends around the open distal end of the housing 66. Shaft housing 66 is the component of the trigger assembly 64 that is physically mounted to the face plate 47. When the trigger assembly 64 is so mounted, lip 68 seats in a recess formed around a hole in the face plate 47 in which the shaft housing 66 is seated. The shaft housing 66 is further formed to have a forward section 70, the section from which lip 68 extends, that has an outer diameter greater than the outer diameter of the remaining, rearwardly extending main body of the housing 66. Shaft housing forward section 70 is formed to have a radially directed threaded bore 72. Bore 72 is dimensioned to receive a fastener (not illustrated) that extends through the face plate 47 so as to hold shaft housing 66 to the face plate.

Shaft housing 66 is further formed to have a back face 74 that closes the proximal end of the housing. Back face 74 is formed with a generally rectangularly. shaped center opening 75. The back face is further formed to have four peripheral openings, 76, 78, 80 and 82 that are located about the perimeter of the back face that are spaced 90° apart from each other. Openings 76–82, it will be observed, extend into the circumferential side wall that forms the main body of the shaft housing 66.

Figure 6:
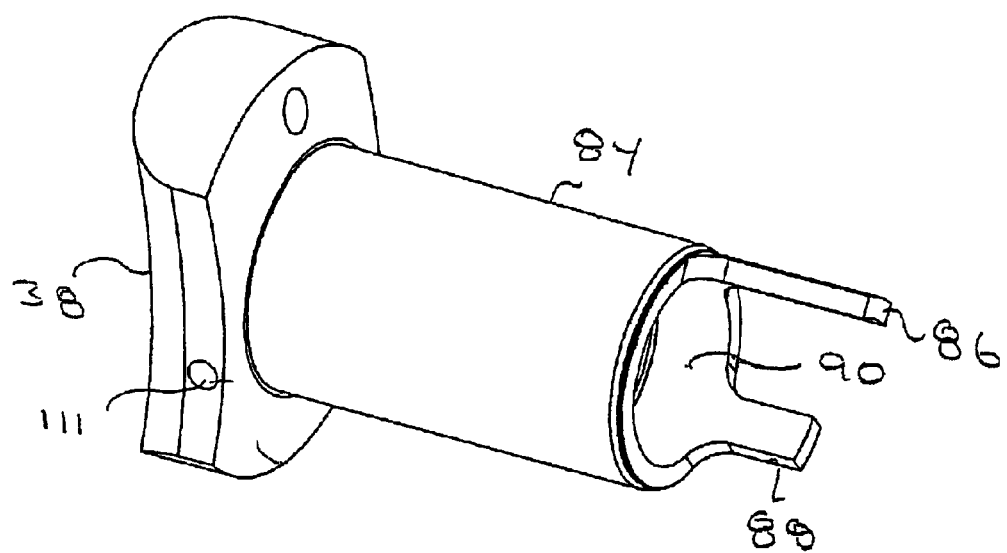
FIG. 6 is a perspective view of the proximal facing end of the trigger and outer shaft of the trigger assembly.

Trigger 38 is formed to be the head end of an outer shaft 84, now described in detail by reference to FIG. 6. The main body of the outer shaft 84 is generally tube-shaped so that it can be slidably fitted in shaft housing 66 and so that it can rotate in the housing 66. The proximal end of the outer shaft is formed to have two diametrically opposed legs 86 and 88. It will be observed that leg 88 is shorter than leg 86. Extending forward of legs 86 and 88, it will be understood that the main body of outer shaft 84 is formed with a bore 90. Bore 90 extends partially into trigger 38. Outer shaft 84 is dimensioned so as to be both seated in the shaft housing 66 and so that a forward section of the main body of the shaft as well as trigger 38 are located forward of the shaft housing.

The outer shaft 84 is fitted over a generally solid, rod like inner shaft 92 also located in shaft housing 66. Inner shaft 92 is shaped to have a stem 93 that is generally rectangularly shaped. More specifically, stem 93 is shaped to slidably extend through center opening 75 of the shaft housing back face 74 without rotating. Washers 87 and 89 are secured to the proximal end of stem 93, the end that extends out of the shaft housing 66 by a threaded fastener 95. Fastener 95 is threaded into a complementary bore 97 in the rearwardly directed face section of the inner shaft stem 93. Washer 87 and 89 are dimensioned to extend over opening 75 so as to prevent the forward movement of the inner shaft 92 out of the shaft housing 66.

Extending forward from stem section 93, inner shaft 92 has a generally circular cross-sectional profile. This forward portion of the shaft 92 is formed with to define an annular groove 96 that is located immediately forward of stem section 93. Groove 96 is dimensioned to accommodate an O-ring,98.

A laterally extending multi-section bore 102 extends through the forward section of the inner shaft. Bore 102 is dimensioned to have a main section dimensioned to accommodate at coil spring 104. At one end, bore 102 has a reduced diameter such that the step between the individual bore sections serves as a stop for one end of the spring. At the opposed end, bore 102 has a larger diameter. This larger diameter portion of the bore 102 is shaped to accommodate therein a ball bearing 106. Immediately rearward of the distally-directed face of the inner shaft 92, the shaft 92 is formed to have a groove 108 that extends around the outer circumference of the shaft. Groove 108 does not extended circumferentially around the outer surface of shaft 92.

When the trigger assembly 64 is assembled, the outer shaft 84 is seated in the inner shaft 92 so that that the forward portion of the inner shaft 92 seats in bore 90. A pin 110 is press fit in an opening 111 in the trigger 38 and extends into bore 90. Pin 110 also seats in groove 108. Pin 110 thus holds the trigger 38 and outer shaft 84 to the inner shaft 92. When the trigger assembly 64 is so assembled, ball bearing 106 seats against an inner wall of outer shaft 84 that defines bore 90. This inner wall is formed to define indentations 112 that are 180° apart from each other. While the inner shaft 92 cannot rotate, outer shaft 84 is capable of rotating relative to the inner shaft. As the outer shaft 84 so rotates, ball bearing 106 goes in and out of registration with the opposed indentations 112. The seating of the ball bearing in each of the indentations 112 provides tactile feedback regarding the orientation of the trigger 38 for purposes to be explained below.

Since groove 108 does not extend circumferentially around inner shaft 92, the material forming the inner shaft blocks the rotation of pin 110 and therefore the rotation of trigger 38 and outer shaft 84. In one version of the invention, trigger assembly 64 is constructed so that the trigger 38 and outer shaft 84 can only rotate 180°. In order to determine the rotational orientation of the trigger 38 to the handpiece, one end of the outer face of the trigger is formed with an orientation dimple 113.

A spring 114 is also disposed in shaft housing 66. Spring 114 extends between the distally directed surface of shaft housing back face 74 and the proximally directed surface of the inner shaft 92 adjacent the distal end of stem 93. Spring 114 provides the biasing force that urges the inner shaft 92, and therefore trigger 38 and outer shaft 84, distally, away from face plate 47. Collectively, the components of the trigger assembly 64 are selected so that, absent any external contrary force, spring 114 holds the shafts 84 and 92 in position so that the shaft legs 86 and 88 are wholly seated within shaft housing 66.

Trigger assembly 64 further includes an O-ring 116 that extends around the main body of the outer shaft 84. O-ring 116 is seated in an annular groove in the shaft housing forward section 70.

The trigger assembly 64 is further formed so that around the open end of the outer housing 66, the housing is formed with a counterbore 118 that surrounds the main bore through which shafts 84 and 92 extend. A variable number of shims 120 are seated in counterbore 118 so as to extend around the shafts 84 and 92. Shims 120 are held in place by a ring 122 that is press fit in the counterbore 118. Owing to the presence of shims 120, ring 122 extends forward a slight distance in front of the distally-directed surface of housing lip 68. Consequently, when trigger 38 is pressed inwardly, towards tool housing 24, the inward movement of the trigger 38 and shafts 84 and 92 is thus limited by the abutment of the proximally directed surface of the trigger against the distally directed surface of ring 122. The significance of this mechanical stop is discussed below.

Figure 7A:
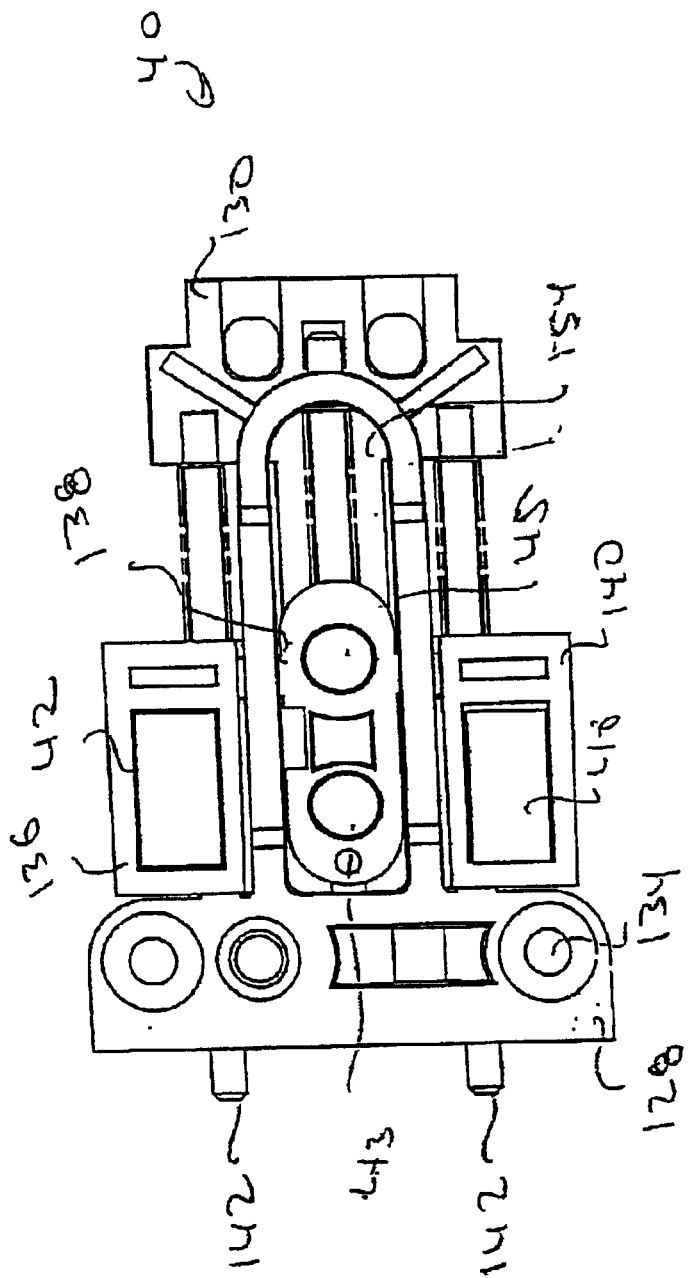
FIGS. 7A and 7B are, respectively, top and exploded views of the carriage assembly.
Figure 7B:
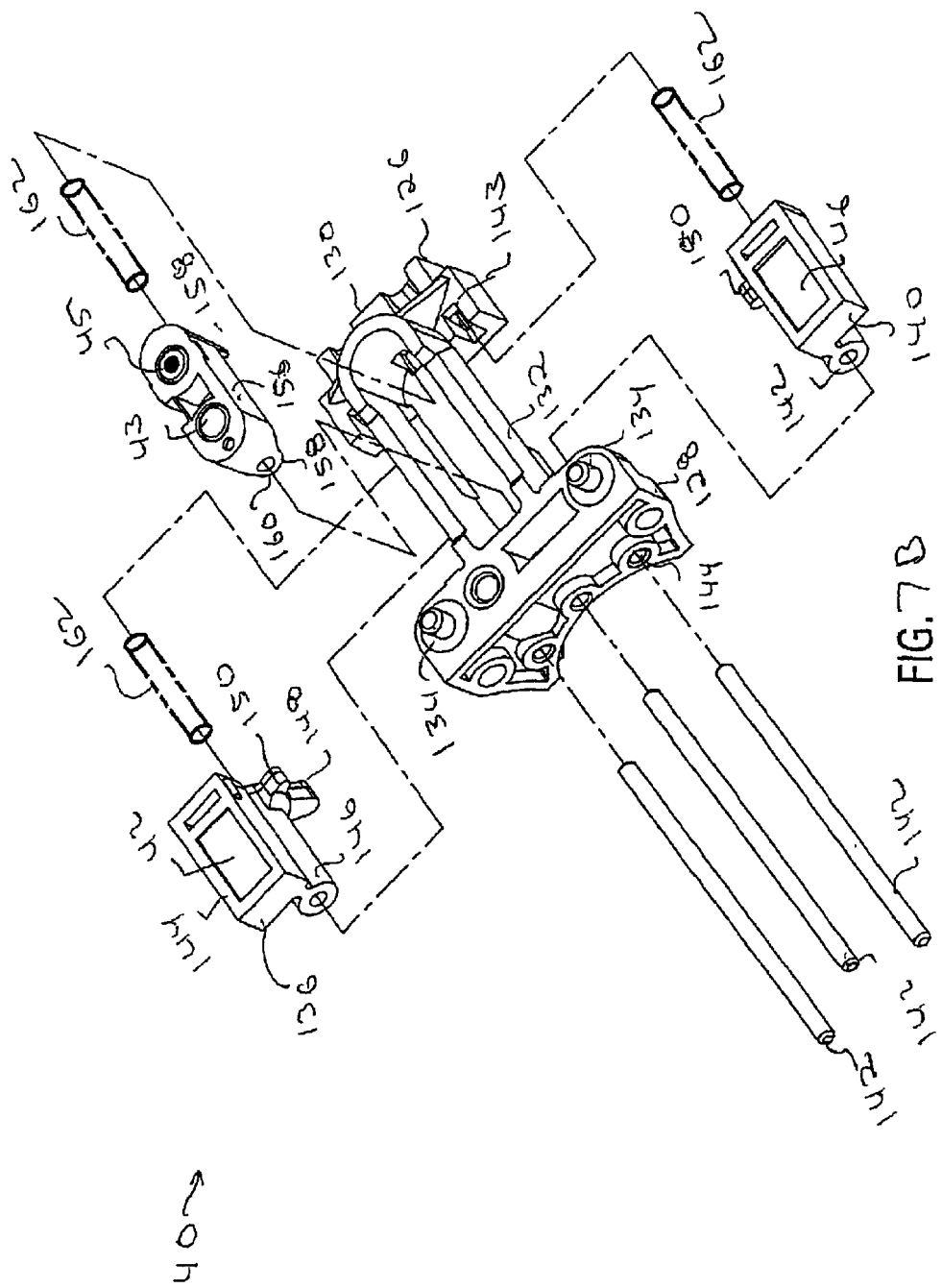

Carriage assembly 40, the assembly to which magnets 42, 44 and 46 are mounted, is now described by reference to FIGS. 7A and 7B. The carriage assembly includes a plastic, approximately H-shaped frame 126. Generally, frame 126 consists of a head end 128, a tail end 130 that is spaced from and extends generally parallel to the head end and a center beam 132 that. connects the opposed ends. Screws, (not illustrated), extend forward from the distally directed face of frame head end 128 and seat in holes in the proximally directed surface of the face plate 47 so as to hold the carriage assembly to the face plate, (face plate holes not illustrated). Pins 134 extend upwardly from frame head end 128. The substrate to which sealed module 48 is mounted seats over pins 134.

Magnets 42, 44 and 46 are mounted in separate carriers 136, 138 and 140, respectively. The carriers 136, 138 and 140 are themselves slidably mounted to individual pins 142 that extend between the head and tail ends 128 and 130, respectively, of frame 126. More specifically, the distal end of each pin 142 is seated in a through hole 144 formed in the frame head end 128. The proximal end of each pin 142 is fitted in a notch 143 formed in the frame tail end 130. The pin 142 to which the center carrier, carrier 138, is mounted is aligned with the longitudinal axis of beam 132. The pins 142 to which carriers 136 and 140 are mounted are spaced laterally away from beam 132.

The pins 142 to which carriers 136 and 140 are mounted also are mounted to frame 126 so as to extend a slight distance forward of head end 128. The distal ends of these pins 142 seat in openings formed in face plate 47 to facilitate the stabilization of carriage assembly 40.

Carriers 136 and 140 are mirror images of each other. Each carrier 136 and 140 has a generally rectangularly shaped body 144 in which the associated magnet 42 or 46, respectively, is housed. Each carrier 136 and 140 also has an elongated sleeve 146 integral with the body 144 that is located along one side of the body and extends longitudinally. Sleeves 146 are the elements of carriers 136 and 140 through which pins 142 extend. Each carrier 136 also has, on the side closest to frame beam 132 a diagonally downwardly extending leg 148 and a diagonally upwardly extending arm 150.

Carrier 138, the carrier in which magnet 44 is housed, is located within an elongated groove 154 formed in the frame center beam 132. In the illustrated version of the invention, carrier 138 actually contains two magnets 43 and 45 that collectively comprise magnet 44. The polarities of the magnets 43 and 45 are reversed so that they collectively produce a magnetic field that is relatively focused and intense. The carrier 138 includes an elongated body 156 in which the magnets 43 and 45 are seated. Feet 158 extend downwardly from the opposed ends of the body 156. Carrier feet 158 are formed with openings 160 so that feet 158 can be fitted over the center located pin 142.

Springs 162 are fitted over pins 142. Each spring 162 extends between the frame tail end 130 and the carrier 136, 138 or 140 mounted to the pin 142 with which the spring is associated. Springs 162 thus bias the carriers towards the frame head end 128 in the absence of any counteracting force. As a consequence of this positioning, the leg 148 of carrier 136 is normally seated in shaft housing bore 76; the leg 148 of carrier 140 is normally seated in shaft housing bore 82.

Carriage assembly 40 is further configured so that the arms 150 of both carriers 136 and 140 abut the distally directed surface of proximal foot 158 of carrier 138. Thus, the proximal movement of either carrier 136 or 140 results in the like displacement of carrier 138.

A surgeon actuates the saw 10 of this invention by rotating the trigger 38 so that the longitudinal axis of the trigger is aligned with the longitudinal axis of the housing 24. The surgeon receives tactile feedback that the trigger 38 and outer shaft 84 are so aligned by the seating of ball bearing 106 in one of the indentations 112. When the trigger is so aligned and, more specifically when it is so aligned and the orientation dimple 113 is in its closest position to the sagittal head 28, output shaft leg 86 is aligned with housing shaft back face bore 76; shaft leg 88 is aligned with back face bore 78. When the trigger 38 and outer shaft 84 are so positioned, pressure can be placed on the trigger to depress it rearwardly. The surgeon actuates the saw 10 by applying finger pressure on the trigger 38 to urge the trigger towards the face plate 47. This movement results in the displacement of shaft leg 86 rearwardly, out of the shaft housing 66 and against the leg 148 of carrier 136. Thus, the rearward movement of the trigger 38, when in this orientation, results in the like displacement of carrier 136 and, therefore, also carrier 138. The rearward movement of magnets 42 and 43 and 45 are detected by sensors 53 and 55. As a result of the change of signal state from sensor 53, motor regulator 60 starts to apply signals to the motor so as to result in the eventual rotation of the motor in the forward direction.

The speed with which motor 26 is to be operated is based on the signal from sensor 55. This signal is a function of the distance between magnet 44 and sensor 55. Sensor 55, motor regulator 60 and speed regulator 61 are configured so that an output signal from the sensor indicating that the magnet 44 is relatively close is interpreted by the regulators as an indication the motor is to be operated at a relatively high speed.

However, as discussed above, trigger 38 abuts ring 122 to prevent the complete depression of the trigger. This stoppage thus limits the extent to which magnet 44 is able to move towards sensor 55. The end consequence of this restriction in movement of the trigger is that the maximum speed at which the motor regulator will allow the motor to run is less than its free speed, the no load speed. It should be understood that this "no-load speed" is the maximum speed for the handpiece motor 26 based on the maximum voltage that can be supplied by battery 25. For example, in one particular version of this invention, it is anticipated that the motor may have a no load speed of between 15,000 and 30,000 RPM. In this version of the invention, the saw 20 of this invention is constructed so that when the trigger is aligned as described above, the maximum speed of the motor is between 30 and 70% of its no load speed. In more preferred versions the no load speed of the motor is between 18,000 and 24,000 RPM and/or the limited maximum speed is between 40 and 60% of the no load speed.

Figure 8:
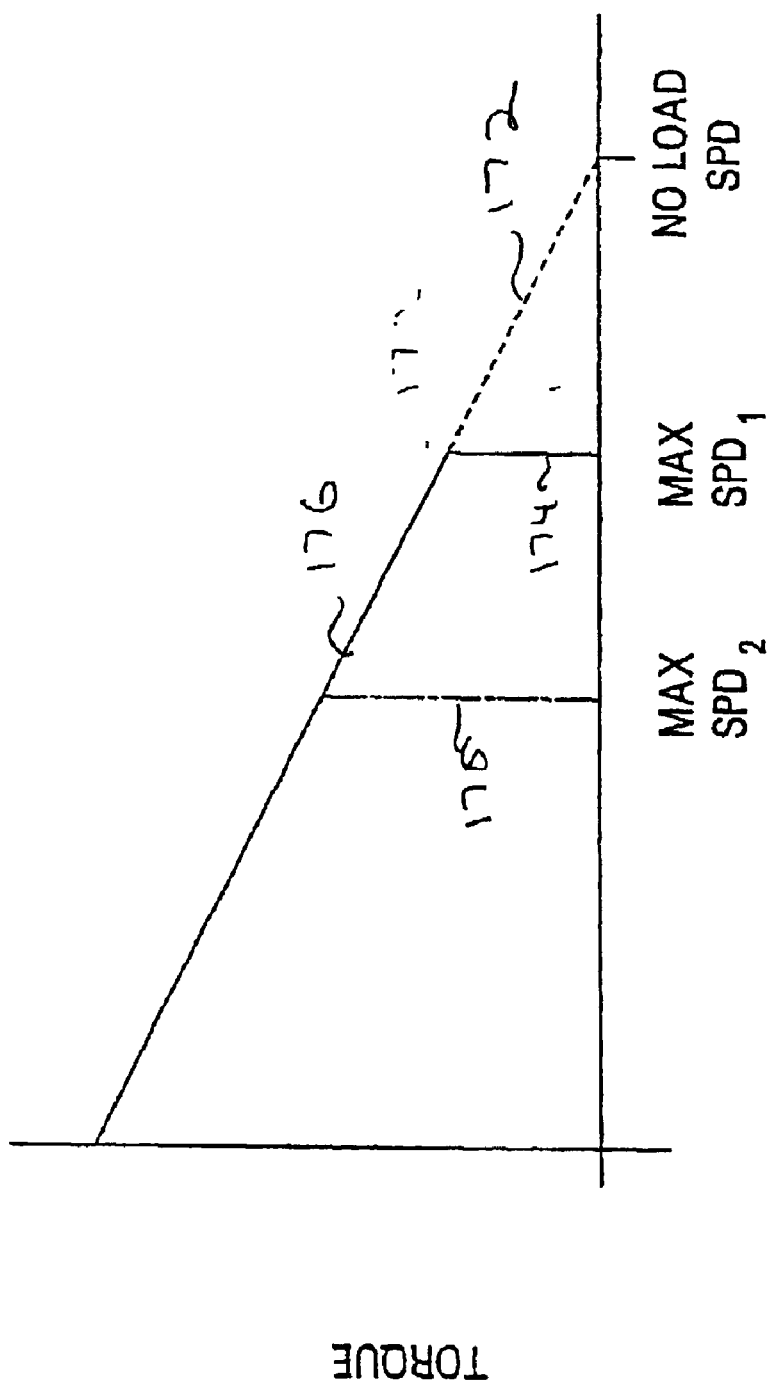
FIG. 8 is a graph depicting the speed torque curves of the powered surgical tool of this invention.

A consequence of this speed limiting of the motor 26 is understood by reference to FIG. 8. Typically, a tool is actuated so that the motor will run at the no-load speed and, then, the cutting accessory coupled to the tool is pressed against tissue. The movement of the moving cutting accessory against tissue causes the motor to apply a torque to the accessory. Given that the energy available to actuate the motor is limited, the production of torque results in the immediate slowing of the speed at which the rotor shaft is able to turn as represented by dotted line segment 172.

However, the tool 20 of this invention is constructed to speed limit the maximum speed of the motor. Thus, even when the tool 20 is not being used to produce torque, due to the limiting affect ring 122 has on the displacement of trigger 38, the surgeon can only set to run the motor at a limited maximum speed (MAX SPD1 in FIG. 8), that is less than the no load speed. When the tool 20 is in this state, and the complementary cutting accessory is pressed against tissue, the motor will produce torque as before. However, because the speed of the motor is less than the no load speed, the battery will, for the given power setting, have power available to continue to energize the motor. Thus, the speed regulator 61 is able to apply energization signals to the motor 26 so that the motor is for some relatively low torque applications, able to run at the limited maximum speed, as represented by line segment 174. In other words, the speed regulator 61 provides closed loop speed regulation of the motor based on the actual motor speed, and the signal representative of user-selected speed even as the load applied to the motor 26 varies.

Eventually though, as the amount of torque the motor is required to produce increases, the motor speed will start to drop as represented by diagonal line segment 176.

Alternatively, the surgeon may, prior to using the tool 20, decide the tool does not have to be operated at a speed as high as MAX SPD1. If the surgeon makes this decision, prior to actuating the tool, he/she rotates trigger 38 and outer shaft 84 around inner shaft 92. This rotation is possible because pin 110 is able to rotate in the inner shaft groove 108. The surgeon stops rotating the trigger 38 when it is oriented 180° from its initial rotation; the trigger is longitudinally aligned with housing 24. Visual observation is obtained of the trigger orientation by the fact that trigger dimple 113 is spaced from the sagittal head 28.

When the trigger 38 and outer shaft 84 are so aligned, shaft leg 88 is in registration with shaft housing back face bore 82; shaft leg 76 is aligned with back face bore 80. The surgeon can depress the trigger to actuate the tool 20. It will be recalled though that shaft leg 88 is shorter than shaft leg 86. Consequently, the trigger 38 and shaft 84 engage in some free travel before these components are depressed enough that leg 88 abuts and starts to displace carrier 140. The overall distance the trigger 38 and the outer shaft 84 can be displaced is constant regardless of the rotational position of these components relative to the rest of the tool 20. Therefore, owing to the relatively short length of leg 88, when the trigger 38 is fully depressed, the leg 88 will have displaced carrier 140 a shorter distance than the distance leg 86 was able to displace carrier 136 when the trigger was similarly depressed.

The minimal displacement of carrier 140 results in magnet 46 being placed in sufficient proximity to sensor 57 so that the sensor undergoes the state change required to cause the actuation of the tool motor 26. However, the limited displacement of carrier 140 results in a like reduced displacement of carrier 138 and magnet 44. The limited displacement of magnet 44 is monitored by sensor 55. The sensor 55 therefore only produces an output signal to cause the motor regulator to run the motor at a limited maximum speed that is even less than the maximum speed for the tool when in the high speed setting, MAX SPD2 in FIG. 8. In the disclosed version of the invention, the motor shaft, when actuated based on the detected displacement of magnet 44, will rotate in what can be considered the reverse direction. However, for the reasons set forth above, this does not affect the back-and-forth movement of blade 31.

Thus, tool 20 of this invention is constructed so that when trigger 38 is fully depressed, the motor 26 will be actuated at a maximum speed that is less than the motor no load speed. As a consequence of this reduced speed maximum speed operation of the motor, the frequency with which linkage assembly 30, coupling head 32 and the attached cutting accessory oscillate back and forth is likewise reduced. One benefit of this reduced oscillation is that less noise is generated by the saw and cutting accessory as a result of its maximum speed operation. A second benefit of this reduced oscillation is that the wear of the components that engage in this motion is likewise reduced. This wear reduction serves to increase the lifetime of these components.

While the maximum speed of the saw is reduced, this reduction does not adversely affect the saw's efficiency for performing a surgical procedure. This is because when the saw is running at the maximum speed and the cutting accessory is applied to a surface and torque is produced, the speed regulator causes additional power to be supplied to the motor so as to maintain the speed. Thus, the power tool will apply the same cutting power supplied by other tools but when a no load state is less noisy.

Another feature of the power tool of this invention is that by the simple rotation of trigger 38, the maximum speed of the tool can be set to a relatively high limit or a relatively low limit. Thus, in a situation in which the surgeon does not require high speed operation of the tool and would prefer quieter operation, the trigger can be set to cause the motor to run at a relatively low maximum speed. An additional advantage for operating the motor at a lower speed is noted by dot-and-dash line segment 175 of FIG. 8. Since the maximum speed of the motor is reduced in comparison to MAX SPD1, the amount of torque the motor will be able to develop before the surgeon notices an appreciable speed drop off increases.

Alternatively, where a surgeon would prefer or require higher speed operation, the trigger is easily reset so that, when the trigger is fully depressed the motor will run at a higher maximum speed. Thus, the single tool of this invention eliminates the need that sometimes arises to provide two similar powered tools that only vary in the maximum speed of their motors.

In the above-described version of the invention, as part of the assembly of tool 20, shims 120 are placed in face plate counterbore 66. More specifically, the appropriate number of shims 120 are fitted in the counterbore 66 so that ring 122 extends forward of the face plate 47 a sufficient extent to cause the appropriate limiting of trigger displacement that, in turn, will result in the motor being caused to operate at the desired limited maximum speed.

Figure 9:
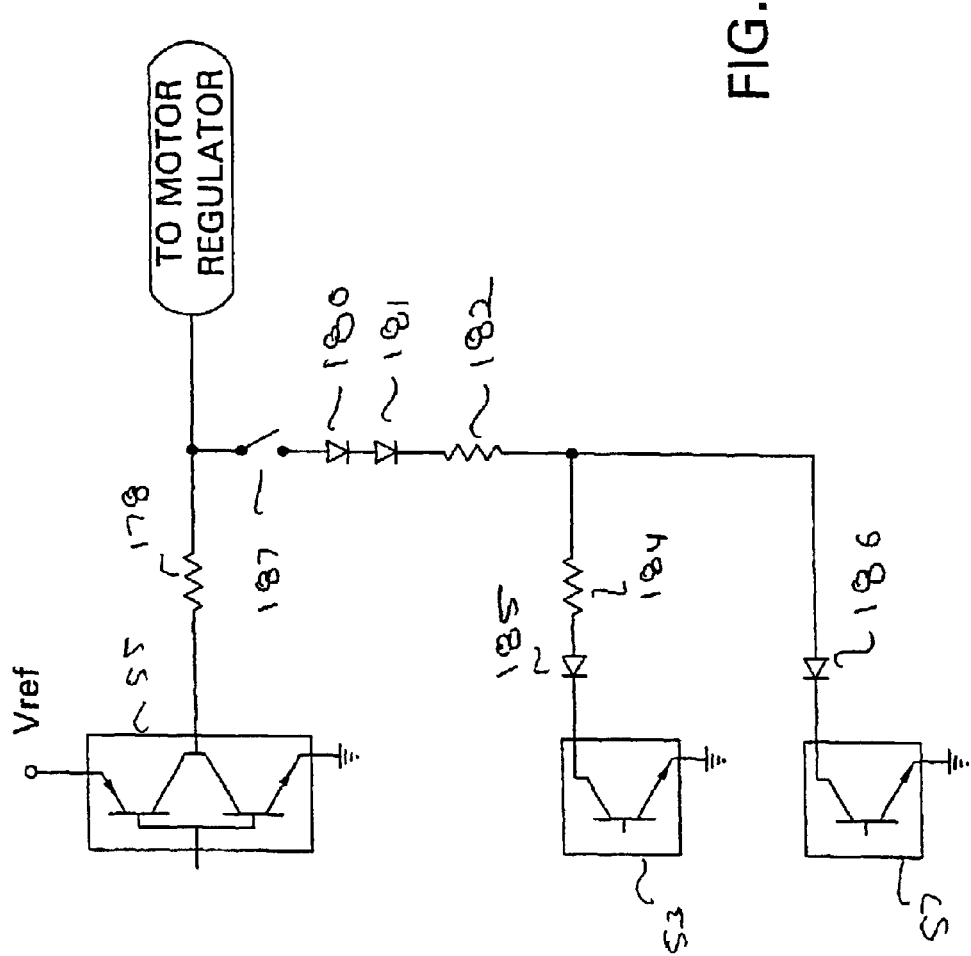
FIG. 9 is a schematic view of components integral with an alternative control circuit of an alternative version of this invention.

FIG. 9 is a schematic diagram of an analog circuit that can be employed as a speed limiting and maximum speed select circuit of this invention. In this version of the invention, the voltage present at the output of sensor 55, the Hall effect sensor, is the signal representative of the user desired speed. This voltage is attenuated by application to a voltage divider before being applied to the motor regulator 60 and speed regulator 61. Specifically, two resistors 178 and 182 are series-connected to the emitter of sensor 55. Two diodes, 180 and 181 are series-connected between resistors 178 and 182. (A switch 187 is located between resistor 178 and diode 180. The purpose of this switch 187, which should normally simply be considered closed, is discussed below.) The free end of resistor 182, the end furthest from sensor 55, is connected to the collector of sensor 53 through a third resistor 184 and a forward biased diode 185. The same end of the resistor 182 is also tied to the collector of sensor 57 through a forward biased diode 186. The emitters of sensors 53 and 57 are both tied to ground.

The voltage present at the junction of resistors 178 and diode 180 is the signal applied to the motor regulator and speed regulator as the signal representative of the user desired speed.

The trigger assembly with which this version of the invention is employed does not have the mechanical stop, shims 120 and ring 122, of the first described version of the invention. Also, in this version of the invention, the outer shaft is designed so that shaft legs 86 and 88 are of identical length. Thus, in this version of the invention, regardless of the relative orientation of trigger 38, when the trigger is depressed, the center magnet 44 is displaced the same amount.

In this version of the invention, when the trigger 38 is set to the highest maximum speed orientation, magnet 42 moves towards sensor 53; magnet 46 is not similarly displaced. As a result of this displacement, only sensor 53 undergoes a state transition. Specifically as a result of this transition, sensor 53 closes so as to tie the series circuit of resistors 178, 182 and 184 to ground. As a result of this circuit being tied to ground, the voltage present at the junction of resistor 178 and diode 182, which is less than and proportional to the output signal from sensor 55, is the voltage applied to the motor regulator and speed regulator 60 and 61, respectively. Since this voltage will always be less than the maximum voltage output from sensor 55, even when trigger 38 is fully depressed, the speed regulator will always cause the motor to run at a limited maximum speed that is less than the no-load speed.

Alternatively, trigger 38 may be oriented to cause the motor to run in the low limited maximum speed state. When the trigger is then depressed, magnet 46, not magnet 42, is the magnet that is similarly displaced. As a consequence of this movement, sensor 57, not sensor 53, undergoes the open-to-closed state transition. This state transition ties the series circuit of only resistors 178 and 182 to ground. Given the changes in the resistance of the sensor 55-to-ground voltage divider, the voltage present at the junction of resistor 178 and 182 is less than the voltage present at this junction when magnet 44 undergoes a like displacement and trigger 38 is in the high speed maximum speed setting. The reduction of this voltage causes speed regulator 61 to, in turn, actuate the motor so that it runs at the lesser of the two maximum speeds.

An advantage of the foregoing version of the invention is that one can set the maximum speed setting of the motor by the selection of precision resistors or the trimming of resistors. This eliminates the need to have to select mechanical parts, such as shims and a nut, to serve as a mechanical stop. This version of the invention also eliminates the need to have precision shape the legs of the outer shaft 84 so that when it is placed in the low speed maximum speed setting, the desired lower maximum speed will be obtained.

Still another advantage of this version of the invention is that in this version of the invention, when the trigger 38 is in the low speed maximum speed setting and is depressed, the motor 26 will start to be actuated at the same point in travel as when in the high speed setting. This eliminates the possibility that the surgeon will be momentarily disconcerted due to the fact that, during the initial displacement of the trigger 38, the motor is not actuated.

Another advantage of the invention described with respect to FIG. 9 is that the diodes 180, 181 and 185 or 186, compensate for signal drift caused by temperature changes of the internal circuitry of the tool 20. In particular, the output signals of both sensor 55 and the tachometer internal to the speed regulator 61 tend to rise as a function of the tool being relatively warm. Generally, there are two reasons the tool may be warm. First, as part of the process of sterilization of the tool 20, it is autoclaved. Sometimes, after the tool is autoclaved it may be used before its temperatures cools to that of the ambient environment. Secondly, the heat generated by motor 26 may warm the other components of the tool 20 to a level at which the output signals from the sensor 55 and tachometer start to drift. If the signals from these components drift, the voltage drops across the diodes 180, 181 and 185 or 186 engage in a like drift in an opposite polarity. Thus, the diodes compensate for temperature induced variations in the signal present at the output end of resistor 178 that would otherwise occur.

As mentioned briefly above, the above circuit may be provided with some sort of switch or jumper, represented by switch 187, between resistor 178 and diode 180. This connection may be provided so that, during manufacturing, the circuitry connected between the switch 187 and ground may be selectively installed or removed from the handpiece. Thus, a single subassembly can be provided that has the circuitry for performing the speed limiting and limited maximum speed speed select feature of this invention or that does not include this feature.

It should be understood that the foregoing description is directed to specific versions of the invention and that other versions of the invention may vary from what has been described. For example, there is no requirement that any one of the features of this invention be solely incorporated into a powered surgical saw and/or solely incorporated into a cordless tool. Thus, one or more features of this invention may be incorporated into an alternative powered surgical tool such as a drill or wire driver that is actuated by power supplied from a remote control console through a power cord. Similarly, it should be recognized that the saws that incorporate the features of this invention need not solely be saws that move the complementary blades in the sagittal motion. These features of this invention may readily be incorporated into saws that move their complementary blades in reciprocal motion.

Likewise, it should be understood that some powered surgical tools of this invention may not employ electrically driven motors as their power generating units. In these versions of the invention, the power-generating unit may be such a device as a pneumatically driven motor, an ultrasonic surgical tool, a RF or electro cauterization probe, a laser or other heat or light emitting unit. The complementary coupling unit connects an accessory that transfers the energy developed by the power-generating unit to the surgical site.

It should similarly be understood that not all surgical tools of this invention will incorporate both the maximum speed limiting assembly and a limited maximum speed speed select trigger. Some tools of this invention may only be constructed to perform maximum speed limiting and not be provided with a trigger that allows the surgeon to select the limited maximum speed. Another alternative tool of this invention may be provided with a trigger or other control member that can both by placed in a select orientation relative to the handpiece to which it is attached in order to provide an indication of maximum power the unit tool should develop and that, in the selected orientation, be moveable to provide an indication of the amount of power the tool should, at any instant, develop. In some versions of this embodiment of the invention, the surgeon may only be able to set the tool to operate at a single speed, the set speed.

Similarly, while two speed limiting assemblies, one mechanical and one electrical, have been described, it should be recognized that alternative speed limiting assemblies may be incorporated into the powered surgical tool 20 of this invention.

For example, shims may be placed in other locations to limit the travel of trigger 38 and outer shaft 84. In one alternative version, for instance, the shims are placed around the inner shaft stem 93. These shims are dimensioned to be fully enclosed within spring 114. Sufficient shims, as well as a lock nut, are provided around the stem so that retraction of the outer shaft 84 and inner shaft 92 is stopped by the abutment of the proximal most shim, (or proximally positioned lock nut), abutting against the inner surface of shaft housing back face 74. Alternatively, the spring 114 may be fully compressible. In these versions of the invention, shims placed at either end of the spring limit the extent to which trigger 38 can be rearwardly displaced.

Other mechanical maximum speed limiting assemblies of this invention may not even include shims. For example, an alternative mechanical speed limiting assembly may be provided by shaping leg 86 of the trigger assembly outer shaft 84 so that it does not immediately displace carrier 136.

Alternatively, a mechanical speed limiting assembly may be constructed by forming the outer shaft 84 so that it has a groove with two spaced apart longitudinally extending branches and a circumferential section that connects the branches. In this version of the invention, the shaft housing 66 has a pin that is seated in the groove. The branches of the grooves are positioned so that depending on which position the trigger 38 and outer shaft 84 are placed, one or the other grooves is aligned with the pin. The length of the grooves is such that the pin abuts the end of the groove in which it is seated prior to when depression of the trigger results in the complete retraction of the outer shaft. Thus, the pin and grooves function as mechanical stops that limit the displacement of the trigger so as to limit the maximum speed at which the motor 26 can be actuated. As a result of the grooves being of unequal length, when the pin is in the longer groove, the tool can be actuated to run at the higher of the two maximum speeds; when the pin is in the shorter groove it can be actuated to run at the lower of the two maximum speeds.

Alternative electronic speed limiting/maximum speed setting assemblies of this invention can be provided. In one version of the invention, for example, the analog signal from the center sensor, sensor 44, the speed sensor, is digitized. In this version of the invention, the maximum speed is determined based on which of the two maximum speed select sensors, sensor 53 or 57, undergoes a state transition. If the higher speed maximum speed select sensor, sensor 53, undergoes the state transition, a logic circuit internal to the speed regulator 61 sets a signal equal to the maximum speed to the higher of the two maximum speed signals. Alternatively, if sensor 57 undergoes a state transition, the logic circuit sets the limited maximum speed to the lower of the two maximum speeds. The actual setting of this speed may be done in a number of different ways depending on the exact structure of the motor regulator 60 and speed regulator 61. For example, if the speed regulator employs an analog comparator to compare the user-selected speed to the motor speed, the logic circuit could selectively apply an analog signal of selected magnitude to the comparator based on the output of sensor 44 and which one of sensors 53 or 57 underwent a state change. Alternatively, an intermediate output from the logic circuit, based on the same three inputs would be a digital signal representative of the user-selected speed. This signal would be converted to an analog signal before being applied to the comparator.

In other versions of the invention, the digital signal representative of user-selected speed may be compared to a digital version of motor speed in order to provide the requisite feedback signal required to ensure proper operation of the motor.

In these versions, as well as other versions, of the invention, a NOVRAM may be provided that contains data describing selected limited maximum speed or speeds of the motor. In these versions of the invention these data are compared to the actual speed of the motor to ensure that the motor runs at a limited maximum speed less than the no load speed. Also, these data may be used as input variables to determine the user selected speed in combination with the signal that indicates the extent to which the surgeon depressed the tool control member. In versions of the invention in which the motor regulator components are primarily digital components, the data read from the NOVRAM may be processed digitally. Alternatively, the data may be converted into a set of analog signals each of which represents a particular limited maximum speed.

An advantage of providing the limited maximum speed data in a NOVRAM is that data representing different limited maximum speeds can be stored in different NOVRAMs. Thus, a base unit can be provided that has a motor that runs at a very high speed. Then, during the assembly process, a NOVRAM with customer-specific limited maximum speeds can be installed to complete assembly of the completed tool 20. An advantage of this arrangement is that it reduces the number of different parts the manufacturer has to have available in order to provide tools that have different limited maximum speeds.

Similarly, it should be recognized that resistor 182 that forms part of the limited maximum speed voltage divider may not always be a single resistor. For purposes of manufacturing a set of series and/or parallel connected resistors may be provided. Then as part of the assembly process, the signal present at the junction of resistor 178 and diode 180 is empirically set to ensure that the motor runs at the appropriate limited maximum speed. Once this signal is determined, jumpers across the resistors forming resistor 182 are appropriately installed or removed to ensure that these resistors collectively have the appropriate resistance to cause to ensure that the output signal applied to the motor regulator 60 causes the motor to operate at the appropriate speed and does not exceed the desired limited maximum speed. An advantage of providing a set of resistors to form resistor 182 is that an automated wiring machine can perform the signal calibration and resistor installation/removal.

It should likewise be understood that some versions of the invention may include a combination of the above described mechanical and electric assemblies that regulate speed and offer the maximum speed select trigger functions of this invention.

Also, in other versions of the invention, the speed regulator 61 may not engage in closed loop regulation of motor speed that holds the motor speed constant as the load applied to the motor varies. In some versions of the invention, the motor regulator 60 and speed regulator 61 may be configured so as to regulate the motor speed based on three inputs: user-selected speed; motor speed; and load applied to the motor.

Figure 10:
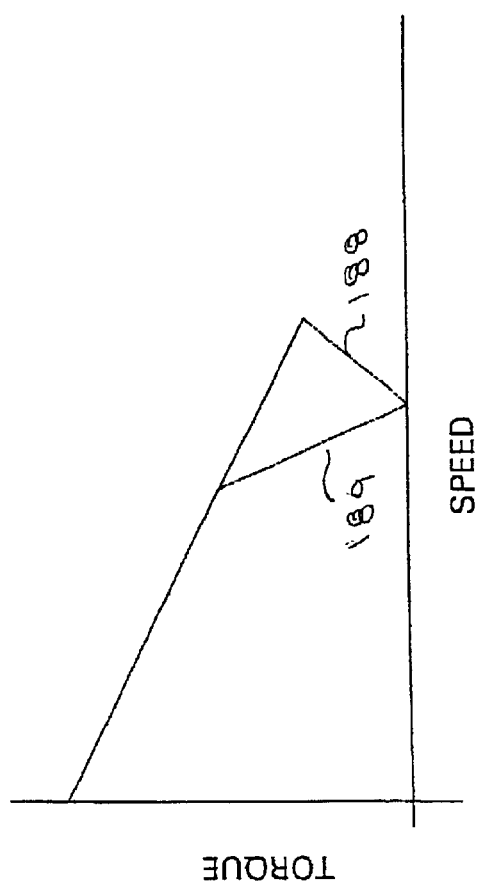
FIG. 10 is a graph depicting alternative speed torque curves of this invention.

This type of speed control is depicted in FIG. 10. Here, line segment of 188 depicts a speed/torque plot that represents how the motor regulator 60 and speed regulator 61 are configured so that, as the motor starts to develop torque the maximum speed undergoes a slight increase before it starts to fall. In still other versions of the invention, the motor regulator and speed regulator may be configured, so that, as depicted by line segment 189, as the motor starts to develop torque there is initially a slight drop in motor speed until, the overall power available to drive the handpiece limits motor speed for the amount of torque that is produced.

Moreover, the actual components forming alternative versions of this invention may be different from what has been described. For example, there is no requirement that all versions of the invention have the trigger, carriage and magnet position sensor assemblies of the described version of the invention. In an alternative version of the invention, the trigger, or other user actuated control member, may be connected to a wiper of a potentiometer internal to the housing 22 that is part of the motor regulator 60. In these versions of the invention, the speed limiting assembly may comprise a mechanical stop that limits the control member from being placed in a position in which the member places the wiper in full speed, no load speed, setting. In the above type of assembly, there is a 1:1 correlation between the movement of the control member and the wiper. In an alternative version of the invention, the drive member between these components may not cause this direct motion. In these versions of the invention, the drive member, like leg 88 of outer shaft 84, maybe configured to inhibit the extent to which the displacement of the control member by the surgeon results in the displacement of the potentiometer wiper to the full speed, no load speed, position.

The foregoing version of the invention can still be provided with a limited maximum speed speed select feature. For example, if the trigger actuates a wiper, the rotational position of the trigger may be used to open/close a switch that establishes the resistance of a voltage divider from which a speed signal or a modified form of the speed signal is applied to the motor regulator and speed regulator.

Also, from the above, it should be recognized that the structure of the control member actuated by the surgeon may vary from what has been described. In not all versions of the invention is this control member a depressible trigger. In some versions of the invention, the control member may be a lever switch that is pivotally connected to the handpiece housing. In still other versions of the invention, the control member may comprise one or more manually actuated electrical switches that are mounted to the outer surface of the handpiece housing. In these versions of the invention, the speed limiting assembly has components internal to the motor regulator and speed regulator that prevent operation of the motor above a maximum speed that is less than the no load speed.

Also, in some versions of the invention, it may be possible to place the trigger in three or more orientations so as to establish three or more maximum operating rates for the associated power generating unit.

Similarly, it should be recognized that the control assembly of this invention need not always include a single control member that is both set to establish the limited maximum speed and the surgeon selected speed. In some versions of the invention, two control members may be provided. For example, a first control member may be employed to establish the limited maximum speed and the second control member is used to establish the surgeon selected speed. In a mechanical version of this embodiment of this invention, the first control member may be a lever or a screw device that limits the extent to which the second control member can be physically displaced. In an electrical version of the invention, the positions of the first and second control members are converted into electrical signals. Based on the positions of these components the motor regulator both sets the surgeon desired speed for the motor and prevents the motor from being driven above the selected limited maximum speed.

Likewise, it should be understood that other means than sensors configured to measure magnetic field strength may be employed as the control member orientation and/or position detecting sensor of this invention. As mentioned above, a potentiometer may function as a sensor that monitors control member position. One or more contact switches may be employed as the sensing components that provide signals representative of control member orientation. Specifically, the control member is connected to the microswitch(es) to open/close the microswitch(es) depending on the orientation of the microswitch.

In still other versions of the invention, the trigger assembly may include optical sensors. In these versions of the invention, each sensed component of the trigger assembly can comprise an always on LED. The complementary sensor is a light sensitive photodiode or phototransistor. Between the LED and sensor is an adjustable shutter. The size of the shutter opening is set mechanically by the trigger as a function of trigger position. Thus, the amount of light that passes through the shutter is a function of trigger position. The photosensor thus generates an output signal representative of trigger position.

Figure 11:
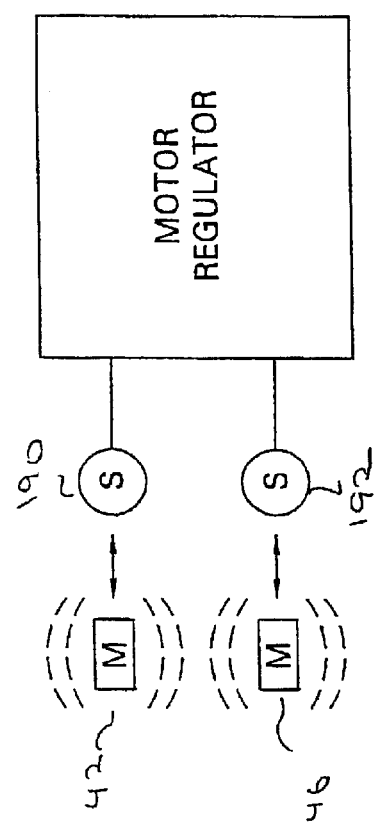
FIG. 11 is a schematic and block diagram of an alternative sensor assembly of this invention.

Alternatively, in some versions of the invention, one or more sensors may perform the function of both indicating the orientation of the control member and the extent to which it is displaced. For example, in some versions of the invention, as depicted in FIG. 11, there may be just two magnets 42 and 46 and complementary sensors, 190 and 192, respectively. When the trigger is in a first orientation and depressed, only magnet 42 is moved. The movement of this single magnet 42 is detected by the complementary sensor 190, hereinafter, the high speed sensor. In response to the change in signal state from the high speed sensor 160, the speed regulator internal to the motor regulator 60*a* causes the motor to run within a first speed range up to a first maximum speed. When slower speed tool operation is desired, the trigger 38, as previously described is reset to the low speed operation. Then, when the trigger is depressed, only a second one of the magnets, magnet 46, is moved. The complementary sensor 192, hereinafter the low speed sensor, detects this displacement. In response to the state change of the output signal from the low speed sensor 192 the speed regulator causes the motor to run within a second speed range up to a second maximum speed. Again, independent potentiometers with wipers that are independently displaced as a function of trigger position could perform the above described dual sensing function.

Similarly, it should be understood that the electrical circuitry employed to apply the energization signals to the motor may be different from what has been described and incorporated herein by reference. Any analog, digital and/or combined analog or digital motor controller that monitors motor speed, receives a signal representative of the user selected speed and, based on these two inputs, applies the energization signals to the motor to cause it to run at the user speed, may be incorporated into the powered surgical tool of this invention.

Thus, it is the object of the appended claims to cover all such modifications and variations that come within the true spirit and scope of this invention.

What is claimed is:

1. A powered surgical saw, said saw including:
    a handpiece;
    a motor disposed in said handpiece for driving a sawblade in a back-and-forth movement at a variable speed in response to a variable energization signal;
    a battery connected to said handpiece to provide energization power to said motor;
    a user-actuated control member movably mounted to said handpiece, said control member being rotatable about an axis between a first orientation and a second orientation, and for each orientation, being displaceable along said axis between an initial position and a final position, with a plurality of user-selected intermediate positions between the initial and final positions, each said position being representative of a user selected motor speed; and
    a speed limiting assembly configured to limit the speed of said motor so that, when said control member is rotated into said first orientation and displaced to said corresponding final position, said speed limiting assembly causes said motor to run at a first maximum speed, and when said control member is rotated into said second orientation and displaced to said corresponding final position, said speed limiting assembly causes said motor to run at a second maximum speed that is less than said first maximum speed.

2. The powered surgical saw according to claim 1, wherein said first maximum speed is equal to or less than a no-load speed.

3. The powered surgical saw according to claim 1, wherein said speed limiting assembly includes a mechanical member connected to said handpiece and which is positioned adjacent said control member such that when said control member is rotated into said first orientation, said mechanical member does not limit displacement of said control member, and when said control member is rotated into said second orientation, said mechanical member limits displacement of said control member by a predetermined amount.

4. The powered surgical saw according to claim 1, wherein said control member is rotatable about said axis into a third orientation wherein said control member in said third orientation is prevented from being displaced along said axis.

5. The powered surgical saw according to claim 4, wherein said third orientation is located between said first orientation and second orientation.

6. The powered surgical saw according to claim 1, further comprising:
    at least one moveable sensed element internal to said handpiece and displaceable between a first position and a second position, wherein displacement of said control member causes displacement of said sensed element between said first position and said second position; and
    a speed regulator configured to regulate the energization of said motor, said speed regulator including at least one sensor configured to wirelessly monitor the displacement of said sensed element;
    wherein said speed regulator energizes said motor to run at a first predefined speed when said sensed element is in said first position, and energizes said motor to run at one of said first maximum speed and second maximum speed when said sensed element is in said second position, and energizes said motor to run at an intermediate speed between said first predefined speed and said one of said first maximum speed and said second maximum speed when said sensed element is in an intermediate position between said first position and said second position.

7. The powered surgical saw according to claim 6, wherein said speed regulator is configured to hold the motor speed at a constant speed as a function of displacement of said control member when a load applied to said motor varies.

8. The powered surgical saw according to claim 6, wherein said sensed element comprises a magnet, and said sensor comprises a magnetic field sensor.

9. The powered surgical saw according to claim 1, further comprising:
    a linkage assembly mounted to said handpiece and connected to a shaft of said motor for converting a rotary movement of said motor shaft to a back-and-forth movement; and
    a coupling assembly mounted to said handpiece and connected to said linkage assembly to engage in back-and-forth movement in response to actuation of said linkage assembly by said motor shaft, said coupling assembly being configured to removably receive said saw blade so that said saw blade engages in back-and-forth movement with said coupling assembly.

10. The powered surgical saw, said saw including:
    a handpiece;
    a motor disposed in said handpiece for driving a sawblade in a back-and-forth movement at a variable speed in response to a variable energization signal;
    a battery connected to said handpiece to provide energization power to said motor;
    a user-actuated control member moveably mounted to said handpiece, said control member being rotatable about an axis between a first orientation and a second orientation, and for each orientation, being displaceable along said axis between an initial position and final position, with a plurality of user-selected intermediate positions between the initial and final positions, each said position being representative of a user selected motor speed;
    a motor regulator connected to said motor and to said battery for selectively applying an actuation signal to said motor, said motor regulator being configured to drive said motor in a first rotational direction when said control member is rotated into the first orientation and subsequently displaced toward said corresponding final position, and to drive said motor in a second rotational direction when said control member is rotated into its second orientation and subsequently displaced toward said corresponding final position; and a speed limiting assembly configured to limit the speed of said motor so that, when said control member is rotated into said first orientation and displaced to said corresponding final position, said speed limiting assembly prevents said motor from running at a speed greater than a first maximum speed, and when said control member is rotated into said second orientation and displaced to said corresponding final position, said speed limiting assembly prevents said motor from running at a speed greater than a second maximum speed that is less than said first maximum speed.

11. The powered surgical saw according to claim 10, wherein said speed limiting assembly includes a mechanical member that connects to said handpiece and which is positioned adjacent said control member such that when said control member is rotated into said first orientation, said mechanical member does not limit displacement of said control member toward said corresponding final position, and when said control member is rotated into said second orientation, said mechanical member limits displacement of said control member toward said corresponding final position by a predetermined amount.

12. The powered surgical saw according to claim 10, further comprising:
three moveable sensed elements that are internal to said handpiece, each of said sensed elements being selectively displaceable between a corresponding first position and a corresponding second position in response to displacement of said control member;
a speed regulator configured to regulate the energization of said motor, said speed regulator including three sensors, each said sensor corresponding to one of said three movable sensed elements and configured to wirelessly monitor displaement of its corresponding sensed element;
wherein a first and second of said three sensed elements are displaced toward their corresponding second positions when said control member is rotated into said first orientation and subsequently displaced towards its corresponding final position, and wherein said second and a third of said three sensed elements are displaced toward their corresponding second positions when said control member is rotated into said second orientation and subsequently displaced towards its corresponding final position; and
wherein detected displacement of said first sensed element by its corresponding first sensor results in said motor regulator being configured to drive said motor in the first direction at a speed equal to or less than said first maximum speed, and detected displacement of said third sensed element by its corresponding third sensor results in said motor regulator being configured to drive said motor in the second direction at a speed equal to or less than said second maximum speed, and detected displacement of said second sensed element by its corresponding second sensor results in energization of said motor to drive same at a speed up to said first or second maximum speed in the corresponding said first or second direction designated by said motor regulator.

13. The powered surgical saw according to claim 12, wherein said sensed element comprises a magnet, and said sensor comprises a magnetic field sensor.

14. A powered surgical tool, said tool comprising:
a handpiece;
a variable speed motor disposed in said handpiece and configured to operate at a select speed in response to the application of a select actuation signal to said motor;
a battery connected to said handpiece to provide energization power to said motor;
a user-actuated control member moveable mounted to said handpiece and selectively rotatable into one of at least two orientations relative to said handpiece, and selectively displaceable between first and second spatial positions relative to said handpiece when said control member resides in one of said at least two orientations;
a sensor assembly disposed in said handpiece, said sensor assembly including:
at least one orientation sensor configured to wirelessly detect when said control member resides in one of said at least two orientations; and
a displacement sensor configured to wirelessly detect an amount of spatial displacement undergone by said control member relative to said handpiece after said control member has been rotated into one of said at least two orientations and displaced from said first spatial position towards said second spatial position;
a motor speed limiting circuit configured to selectively restrict a maximum operating speed of said motor to one or more predetermined speeds in response to said orientation sensor detecting said control member in one of said at least two orientations.

15. The powered surgical tool according to claim 14, wherein said motor speed limiting circuit restricts the maximum operating speed of said motor to a first predetermined operating speed when said at least one orientation sensor detects said control member residing in a first of said at least two orientations;
said motor speed limiting circuit restricts the maximum operating speed of said motor to a second predetermined operating speed when said at least one orientation sensor detects said control member residing in a second of said at least two orientations; and
wherein said first predetermined operating speed is equal to or less than a no-load speed of said motor, and said second predetermined operating speed is less than said first predetermined operating speed.

16. The powered surgical tool according to claim 14, wherein said sensor assembly comprises at least two orientation sensors and a displacement sensor, with a first of said at least two orientation sensors configured to wirelessly detect when said control member is in a first of said at least two orientations, and a second of said at least two orientation sensors configured to wirelessly detect when said control member is in a second of said at least two orientations;
wherein said motor speed limiting circuit restricts the maximum operating speed of said motor to a first predetermined speed when said first of said at least two orientation sensors detects said control member in said first orientation, and restricts the maximum operating speed of said motor to a second predetermined speed different from said first predetermined speed, when said second of said at least two orientation sensors detects said control member in said second orientation.

17. The powered surgical tool according to claim 16, further comprising:
three displaceable carriages disposed in said handpiece, with each carriage mounting thereon a sensed element that can be detected, respectively, by one of said at least two orientation sensors and said displacement sensor;
a first linkage member attached to said control member and which displaces a first of said carriages towards a first of said at least two orientation sensors when said control member is rotated into a first of said at least two orientations and displaced between said first and second spatial positions relative to said handpiece;

a second linkage member that attaches to said control member and which displaces a second of said carriages towards a second of said at least two orientation sensors when said control member is rotated into a second of said at least two orientations and displaced between said first and second spatial positions relative to said handpiece; and a third linkage member that selectively attaches a third carriage to said first and second carriages such that said third carriage is displaced towards said displacement sensor when either said first carriage or said second carriage is displaced, respectively, towards said first and second orientation sensor.

18. The powered surgical tool according to claim 14, wherein said control member is rotatably attached to said handpiece and is movably attached to said handpiece so that a portion of said control member is selectively displaceable between said first and second spatial positions relative to said handpiece; and said displacement sensor is configured to wirelessly detect an amount of spatial displacement undergone by said portion of said control member relative to said handpiece after said control member has been rotated into one of said at least two orientations.

19. The powered surgical tool according to claim 14, wherein selective displacement of said control member between said first and second spatial positions is accomplished by retracting said control member towards, or extending said control member away from, said handpiece.

20. The powered surgical tool according to claim 14, wherein said motor speed limiting circuit comprises a voltage divider circuit.

21. The powered surgical tool according to claim 20, wherein said voltage divider circuit includes;

one of a switch and jumper that can be placed into one of at least two states; and one or more resistors configured to provide one of at least two electrical current resistance values depending on said state of said one switch and jumper.

22. The powered surgical tool according to claim 14, wherein said at least one orientation sensor and displacement sensor output a digital signal, and detection of said control member orientation is indicated by a change in state in the digital signal output by said at least one orientation sensor.

23. The powered surgical tool according to claim 22, wherein said motor speed limiting circuit includes non-volatile memory (NOVRAM) that contains data defining said first maximum speed and said second maximum speed of said motor.

24. The powered surgical tool according to claim 23, wherein said non-volatile memory is configured to be removable and replaceable, such that said first maximum speed and second maximum speed can be selected depending on the non-volatile memory inserted into said motor speed limiting circuit.

25. The powered surgical tool according to claim 14, further comprising a speed regulator configured to regulate a speed of said motor based upon a user selected speed, an actual motor speed, and a motor load.

26. The powered surgical tool according to claim 14, wherein said at least one orientation sensor and said displacement sensor comprise one of a magnetic field sensor and an optical sensor.

27. The powered surgical tool according to claim 26, wherein said user-actuated control member includes at least one magnet configured to be displaced relative to said at least one orientation sensor and displacement sensor when said control member is selectively rotated into one of said at least two orientations and selectively displaced between said first and second spatial positions.

28. The powered surgical tool according to claim 26, wherein said user-actuated control member includes a shutter that directs light upon said at least one orientation sensor and displacement sensor, with a size of said shutter adjusting in response to displacement of said control member between said first and second spatial positions.

29. A powered surgical saw, said saw including:

a handpiece;

a motor disposed in said handpiece for driving a sawblade in a back-and-forth movement at a variable speed in response to a variable energization signal;

a battery connected to said handpiece to provide energization power to said motor;

a user-actuaged control member movably mounted to said handpiece, said control member being displaceable between an initial position and a final position, with a plurality of user-selected intermediate positions between the initial and final positions, each said position being representative of a user selected motor speed; and a speed limiting assembly located on said handpiece and selectively moveable into one of at least first and second states, said speed limiting assembly when in said first state being disposed to restrict displacement of said control member by a first predetermined amount so as to limit an operating speed of said motor to a first predetermined maximum operating speed, and when in said second state being disposed to restrict displacement of said control member by a second predetermined amount so as to limit the operating speed of said motor to a second predetermined operating speed that is less than said first predetermined operating speed.

30. The powered surgical saw according to claim 29, wherein said speed limiting assembly comprises a sleeve that mounts around a shaft of said control member and which can be rotated into one of said first and second states.

31. The powered surgical saw according to claim 29, wherein said user-actuated control member is displaceable along a first axis;

said speed limiting assembly is moveably mounted on said handpiece and configured to be selectively placed into one of said first and second states by displacement along a second axis different than said first axis; and said control member is movably mounted upon said speed limiting assembly such that said control member and speed limiting assembly are collectively displaced along said second axis to one of said first and second states.

32. A powered surgical saw, said saw including:

a handpiece;

a motor disposed in said handpiece for driving a sawblade in a back-and-forth movement at a variable speed in response to a variable energization signal;

a battery connected to said handpiece to provide energization power to said motor;

a user-actuated control member movably mounted to said handpiece, said control member being displaceable between an initial position and a final position, with a plurality of user-selected intermediate positions between the initial and final positions, each said position being representative of a user selected motor speed;

at least one moveable sensed element internal to said handpiece and displaceable between a first position and a second position, wherein displacement of said control member causes displacement of said sensed element between said first position and said second position;

a speed regulator configured to regulate the energization of said motor, said speed regulator including at least one sensor configured to monitor the displacement of said sensed element, said speed regulator energizing said motor to run at a first predefined speed when said sensed element is in said first position, and energizing said motor to run at a second predefined speed when said sensed element is in said second position, and energizing said motor to run at an intermediate speed between said first predefined speed and said second predefined speed when said sensed element is in an intermediate position between said first position and said second position; and a speed limiting assembly located on said handpiece and selectively configured into one of at least first and second states, said speed limiting assembly when in said first state is disposed to restrict displacement of said at least one sensed element by a first predetermeined amount, and when in said second state is disposed to restrict displacement of said at least one sensed element by a second predetermined amount different than said first predetermined amount;

wherein an operating speed of said motor is equal to or less than a first maximum speed when displacement of said at least one sensed element is restricted by said first predetermined amount, and is equal to or less than a second maximum speed when displacement of said at least one sensed element is restricted by said second predetermined amount, with said second maximum speed being less than said first maximum speed.

33. The powered surgical saw according to claim 32, wherein said speed limiting assembly comprises a mechanical sleeve that mounts around a shaft of said control member and which can be rotated into one of said first and second states.

34. The powered surgical saw according to claim 32, wherein
said user-actuated control member is displaceable along a first axis;
said speed limiting assembly is moveably mounted on said handpiece and configured to be selectively placed into one of said first and second states by displacement along a second axis different than said first axis; and
said control member is movably mounted upon said speed limiting assembly such that said control member and speed limiting assembly are collectively displaced along said second axis to one of said first and second states.

35. The powered surgical saw according to claim 32, further comprising:
at least one displaceable carriage disposed in said handpiece and upon which is mounted said at least one sensed element; and
at least one linkage member attached to said control member and which displaces said at least one carriage towards said at least one sensor when said control member is displaced between said initial position and final position.

* * * * *

UNITED STATES PATENT AND TRADEMARK OFFICE
CERTIFICATE OF CORRECTION

PATENT NO. : 6,960,894 B2
DATED : November 1, 2005
INVENTOR(S) : Steve Carusillo et al.

It is certified that error appears in the above-identified patent and that said Letters Patent is hereby corrected as shown below:

<u>Column 19,</u>
Line 33, change "displaement" to -- displacement --.

Signed and Sealed this

Second Day of May, 2006

JON W. DUDAS
*Director of the United States Patent and Trademark Office*